United States Patent [19]

Lee

[11] 4,350,638

[45] Sep. 21, 1982

[54] BRUCEOLIDES

[75] Inventor: Kuo-Hsiung Lee, Chapel Hill, N.C.

[73] Assignee: Research Corporation, New York, N.Y.

[21] Appl. No.: 193,601

[22] Filed: Oct. 3, 1980

[51] Int. Cl.$^3$ ............................................ C07D 493/04
[52] U.S. Cl. .................................................. 549/275
[58] Field of Search ................................... 260/343.42

[56] References Cited

U.S. PATENT DOCUMENTS 3,969,369  7/1976  Kupchan et al. .............. 260/343.42

FOREIGN PATENT DOCUMENTS 1440094  6/1976  United Kingdom ........... 260/343.42

*Primary Examiner*—John M. Ford
*Attorney, Agent, or Firm*—Omri M. Behr

[57] ABSTRACT

There are provided two synthetic routes to the known potent anti-leukemic quassinoid bruceantin from the more readily available bruceoside-A and -B. Certain of the intermediate compounds produced in the synthetic sequence as well as bruceantin itself have been shown to possess anti-malarial properties.

1 Claim, 2 Drawing Figures

BRUCEOLIDES

BACKGROUND OF THE INVENTION

Bruceantin, a potent anti-leukemic quassinoid, is isolated from the Ethiopian *Brucea antidysenterica*. Isolation from this source is difficult and the provision of alternate sources of this material would be desirable.

The more readily available *Brucea javanica* is the source of quassinoid glycosides, bruceoside-A and -B. These materials differ from bruceantin in the presence of a glycoside moiety at the 2- or 3- positions and in a different ester moiety at the 15- position. The conversion of these glycosides to bruceantin would therefore be of interest.

SUMMARY OF THE INVENTION

In one embodiment of the present invention, bruceoside (I) is subjected to mild alkaline hydrolysis followed by acid hydrolysis in an alkanol to provide bruceolide (II). While bruceolide is a known compound, heretofore it has only been available by degradation of bruceantin (V) and therefore could not be considered suitable to provide a plentiful precursor for the synthesis of bruceantin (V). The acid hydrolysis of the aforesaid bruceoside provides brusatol (VIIIa), also previously known, which differs from burceolide (II) in that the methylbutenoyl moiety at the C-15 position is still present. Esterification of bruceolide (II) yields the 3-, 15-, and 3,15-, esters. Certain of these esters have interesting anti-malarial properties against chloroquine resistant parasites.

Where this esterification is carried out with a 3,4-dimethyl-2-pentenoylating agent, there is obtained the corresponding 3,15-bruceolide diester (III) as well as the corresponding 3-bruceolide monoester (IV). This latter compound may be re-esterified to the corresponding 3,15 diester (III).

Acid hydrolysis in alkanol of the diester (III) yields the desired bruceantin (V).

In another embodiment of the invention, the bruceoside is subjected to alkaline hydrolysis only which removes the senecioyl moiety at the 15-position while leaving the glycoside moiety at the 2- or 3-position intact. The alkaline hydrolysis provides a free hydroxyl moiety at the 15-position which is then esterified and the glycoside moiety removed, suitably by means of a Lewis acid. Where the esterifying agent is a 3,4-dimethyl-2-pentenoylating agent, the product is bruceantin (V).

It should be noted that in both of these embodiments regardless of whether bruceoside-A or bruceoside-B are the starting materials, the final product is a 3-hydroxy-$\Delta^3$-2-ketone.

There is also provided a synthesis of 3,4-dimethyl-2-pentenoyl chloride (IX) which comprises subjecting methylisopropyl ketone (XII) to a Wittig reaction with triethylphosphonoacetate, subjecting the thus produced ethyl 3,4-dimethyl-2-pentenoyl ester (XI) to alkaline hydrolysis to provide the corresponding carboxylic acid (X) which is then treated with thionyl chloride to provide the desired acid chloride (IX).

Most surprisingly it has been found that the aglycones produced in accordance with the present invention have activity against chloroquine resistant human malarial parasites.

BRIEF DESCRIPTION OF THE DRAWINGS

FIG. I shows a flow chart of one preferred embodiment of the invention.

FIG. II shows a flow chart of a second preferred embodiment of the invention.

DESCRIPTION OF THE PREFERRED EMBODIMENTS

Figure 1:
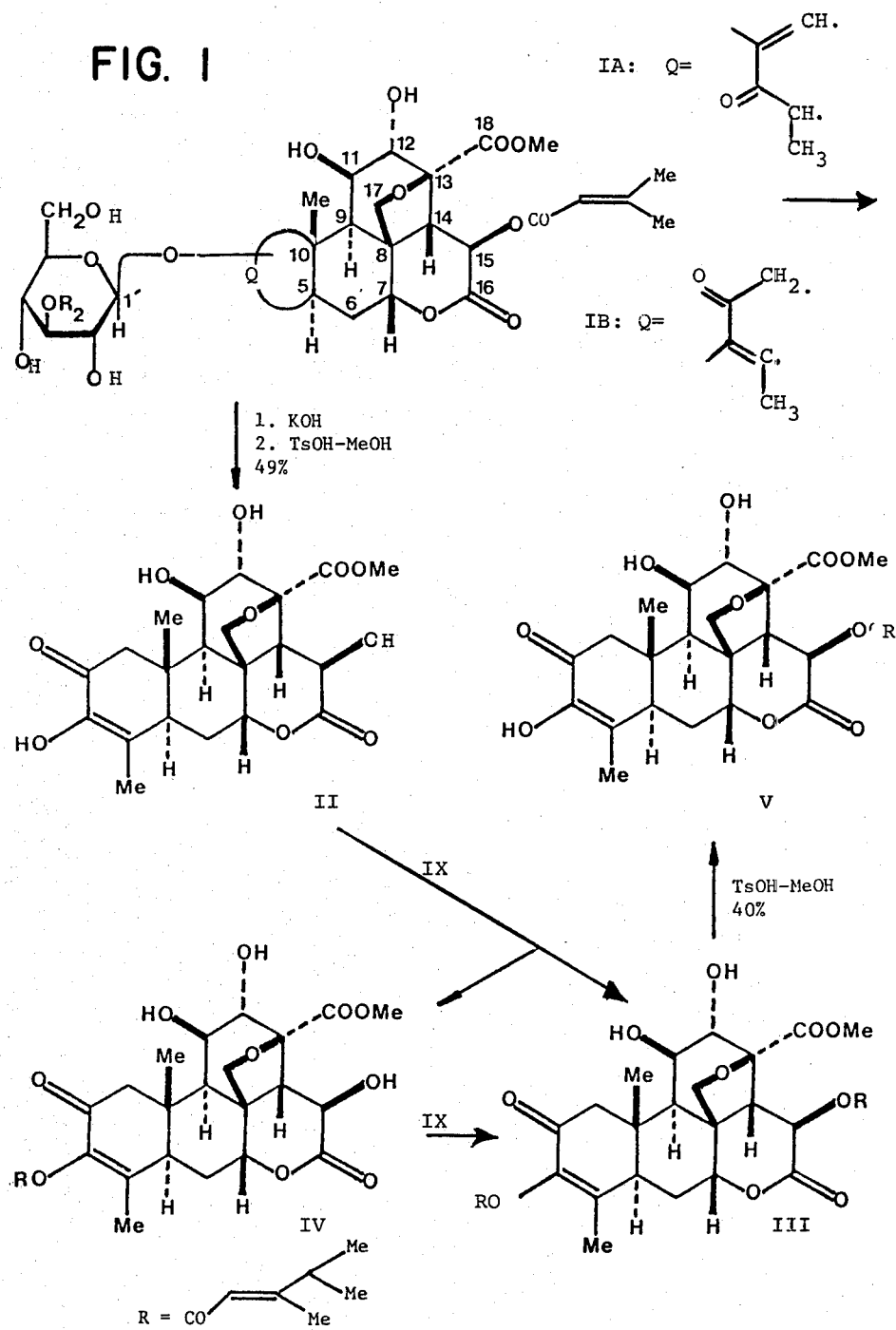
Figure 2:
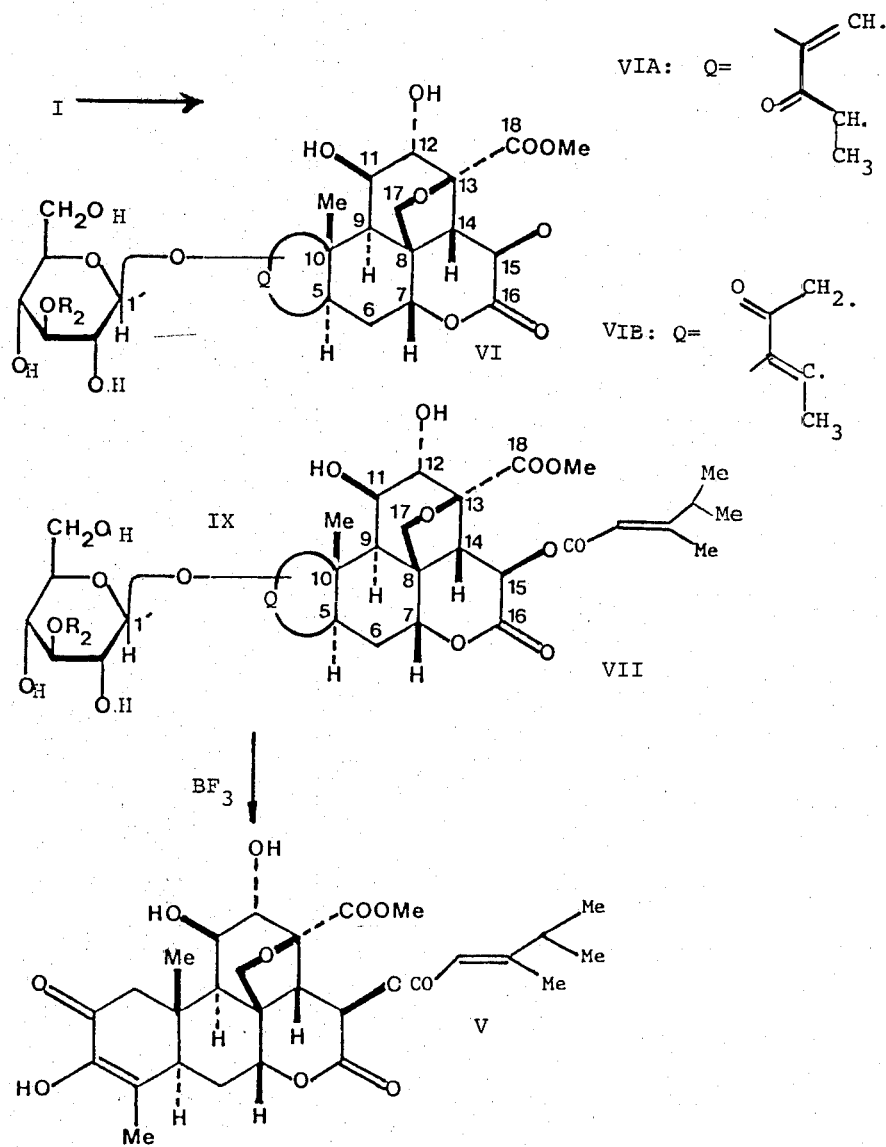

The starting material of the present invention is the known quassinoid glycoside bruceoside (I) which is obtainable in the -A and -B isomers in good yields from *Brucea javanica* (Lee et al., *J. Chem. Soc., Chem. Commun.* 69 (1977) and Lee et al., *J. Org. Chem.* 44, 2180 (1979)). The starting material is subjected to mild hydrolysis in alkali, suitably methanolic alkali. Mild conditions, suitably between about −5° C. to about 20° C., most suitably about 0° C., are desirable using a solution of between 0.5 and 2 N potassium or sodium hydroxide. Under milder conditions of concentration and temperature, the reaction is too slow to be practical and under more vigorous conditions, particularly at ambient temperatures and above, the lactone ring between the 7- and 16-positions is in danger of opening which would cause several synthetic problems, and the ester at C-13 is partially hydrolyzed. This latter problem however is not serious and can readily be overcome by remethylation.

The reaction mixture is neutralized either by the addition of sufficient acid, suitably aqueous mineral acid to precipitate out the alkali as salt, or by contact with a suitable cation exchange resin. The mother liquor is concentrated under reduced pressure and dissolved in alkanol, suitably methanol, and heated under reflux in the presence of an approximately equimolar amount of organic acid, suitably p-toluenesulfonic acid. The reaction mixture is then worked up in the usual manner and purified, suitably by preparative scale thin layer chromatography to yield bruceolide (II) in good yield.

The thus produced bruceolide (II) is then subjected to esterification suitably with an acid chloride in the presence of a base. It is preferred to utilize a substantial excess, suitably between 4 and 7 moles of acid chloride, in a suitable reaction inert anhydrous organic solvent suitably halogenated solvent such as chloroform, per mole of bruceolide (II) in an anhydrous organic base such as pyridine. The reaction is carried out initially at a low temperature suitably between −5° C. and 10° C. and thereafter heated for about 24 hours at moderately elevated temperatures, that is to say, not above the boiling point of the organic solvent, for example, between about 40° C. and 70° C. The reaction mixtures is then worked up in the usual manner and purified, suitably by preparative scale thin layer chromatography, to yield a mixture of the 3,15-diester and the 3-monoester. The monoester is separated and then, if desired, re-esterified by the same procedure to yield the diester in good yield. Where it is desired to ultimately produce bruceantin, the esterifying agent is a 3,4-dimethyl-1-pentenoylating agent, such as 3,4-dimethyl-2-pentenoyl chloride (IX). Other esterifying agents may be employed to provide the antimalarial compounds within the scope of the present invention. These include cinnamoylating agents, benzoylating agents, trimethoxybenzoylating agents, acetylating agents, succinoylating agents, and glutaroylating agents, suitably in the form of the appropriate halides for example, the acid chlorides.

Starting with bruceolide (II) there are thus produced the corresponding 3-cinnamate, 3-benzoate, and 3-trimethoxybenzoate, and the corresponding 3,15-dicinnamate, 3,15-dibenzoate and 3,15-di(trimethoxybenzoate).

The thus produced 3,15-diester may be readily converted to the corresponding 15-ester by acid hydrolysis. Due to the stereochemistry of the basic skeleton, the rates of hydrolysis of the ester moieties attached to the 3-, 13- and 15-positions are different. It is desirable to provide conditions which will leave the 13- and 15-position ester moieties intact while removing the ester moiety at the 3-position. It has been found that a strong organic acid such as p-toluenesulfonic acid in an alkanol most suitably in methanol, provides a satisfactory hydrolytic medium. Heating p-toluenesulfonic acid under reflux in methanol is especially preferred, although the same reagent in higher alkanols is also operative.

By this mode, bruceantin (V) is prepared from the 3,15-di(3,4-dimethyl-2-pentenoyl) bruceolide (III).

Similarly, the corresponding C-15 cinnamate, benzoate or trimethoxybenzoate may be produced from the corresponding 3,15-diester.

In an alternate embodiment of the present invention the senecioyl moiety at the 15-position of the bruceoside (I) is removed while initially leaving the glycoside moiety intact. In this procedure the bruceoside is treated with alkali, suitably potassium or sodium hydroxide in alkanol, suitably in methanol, at a low temperature preferably between −5° C. and ambient temperature.

After completion of the hydrolysis, the reaction mixture is neutralized either by the addition of a neutralizing amount of aqueous mineral acid suitably dilute sulfuric acid or by contacting with a suitable cation exchange resin.

Where the hydrolysis is carried out at a temperature closer to room temperature than 0° C., the methyl ester group at C-13 is partially hydrolyzed. Should this occur, as is readily determined by spectroscopic investigation, the carboxyl moiety is remethylated with diazomethane in the usual manner.

The thus produced 15-desenecioyl bruceoside (VI) (-A or -B as the case may be) may, if desired, be subjected to acid hydrolysis to yield the bruceolide (II). However, it is preferred to esterify compound (VI) in the same manner as discussed hereinabove to provide the corresponding 15-desensioyl bruceoside 15-ester. The glycoside moiety is then removed by treatment with a Lewis acid. Preferred among the Lewis acids is borontrifluoride/etherate. There is thus produced, depending upon the ester group at the 15-position, bruceantin (V) or any of the other corresponding 15-esters mentioned above.

Acid hydrolysis of bruceoside-A or -B yields brusatol (VIIIa), a compound of structure analogous to bruceolide (II) but carrying a senesioyl moiety at the 15-position. This ester moiety may be hydrogenated to form the corresponding dihydrobrusatol (VIII-b).

Utilizing procedures similar to those set forth above, brusatol (VIIIa) may be esterified to form esters having antimalarial activity. Brusatol (VIIIa) may be reacted with bifunctional carboxylic acid moieties such as succinoyl chloride or glutaroyl chloride to provide the corresponding bisbrusatolyl esters, such as bisbrusatolyl succinate or bisbrusatolyl glutarate. Utilizing somewhat more vigorous conditions of esterification, the corresponding C-3, C-11 and C-12 triesters may be formed, suitably the corresponding lower alkanoate, preferably having from 1 to 5 carbon atoms such as the triacetate.

The 3,4-dimethyl-2-pentenoyl chloride (IX) utilized in the procedures of the present invention may be readily prepared from 3-methyl-2-butanone (XII) utilizing the Wittig reaction. In this procedure triethylphosphonoacetate is added to a suspension of sodium hydride in diglyme in an inert atmosphere at a temperature of between −10° C. and 5° C., suitably about 0° C. The mixture is stirred, suitably for about half an hour, to ensure formation of the Wittig reagent and the ketone (XII) added slowly thereto. There is utilized approximately 100% molar excess of the triethylphosphonoacetate with respect to the ketone (XII). The reaction is completed by allowing the reaction mixture to equilibrate with room temperature after completion of the addition, and remaining at ambient temperature from between 2 to 5 hours. The mixture is then recooled and carefully quenched with a large excess of water and the reaction product extracted therefrom with a reaction inert water insoluble organic solvent, suitably ether and the thus produced ethyl 3,4-dimethyl-2-pentenoate (XI) isolated from the ethereal extract in the usual manner.

The ethyl ester is then hydrolyzed, suitably with aqueous alkali, by heating at a temperature somewhat below the boiling point of water, suitably on a steam-bath, until no oily supernate was noted. The reaction mixture, comprising 3,4-dimethyl-2-pentenoate salt in solution is then acidified and the corresponding acid (X) extracted and isolated in the usual manner.

The thus produced acid (X) is then heated to boiling with excess thionyl chloride in a suitable anhydrous reaction inert organic solvent, such as benzene, until the evolution of hydrochloric acid gas ceases. The volatile components, that is to say, the solvent and the excess thionyl chloride are removed under reduced pressure and the 3,4-dimethyl-2-pentenoyl chloride (IX) purified by distillation.

The 3-, 15-esters and 3,15-diesters of bruceolide of the present invention, including bruceantin as well as brusatol and bruceolide, are effective inhibitors of chloroquine resistant strains of the malarial parasite *Plasmodium falciparum* and may be administered in amounts and dosage forms corresponding to those required to inhibit the non-chloroquine resistant strains.

EXAMPLE I

Bruceolide II

Bruceoside-A (I, 4.1 g. 6.01 mmol), was dissolved in potassium hydroxide/methanol solution (1 N, 100 mL) under cooling at 0° C. and stirred at the same temperature for 15 min. The reaction mixture was neutralized with aqueous sulfuric acid (12 N) under cooling and the salt formed by the procedure was removed by filtration. The mother liquor was concentrated under reduced pressure and the residue was dissolved again by addition of methanol (25 mL). Thereafter p-toluenesulfonic acid (1 g, 5.81 mmol) was added to the solution and the mixture heated under reflux for 19 hours.

The reaction mixture was subjected to preparative thin layer chromatography [Chloroform-Acetone (1:1, v/v)] to give bruceolide (II, 1.33 g, 49% yield, white crystals): mp 308°-309° (lit. mp 300°-302°); $[\alpha]_D^{25}-78.3°$ (c 0.45, pyridine) (lit. $[\alpha]_D^{25}-92.5°$ (c 0.18, pyridine). The spectral (IR, NMR and mass) data of II were in accordance with those reported for bruceolide. (Kupchan et al., J. Org. Chem. 40, 618, 1975).

In accordance with the above procedure, but utilizing bruceoside-B in place of bruceoside-A, the same product is obtained.

EXAMPLE II

Ethyl 3,4-dimethyl-2-pentenoate (XI)

To a suspension of sodium hydride (2.6 g) in diglyme (10 mL) triethylphosphonoacetate (24 g, 107 mmol) was added dropwise under nitrogen in an ice bath (ca. 0° C.). The mixture was stirred for 30 min. and then 3-methyl-2-butanone (XII, 4.3 g, 50 mmol) was added dropwise and the mixture stirred at ambient temperature for three hours. The mixture was cooled, diluted cautiously with a large excess amount of water, and extracted with ether. The ethereal extract was dried over anhydrous magnesium sulfate, filtered and evaporated in vacuo to yield ethyl 3,4-dimethyl-2-pentenoate (XI, 7.1 g, 91%): NMR (Jeol C 60 HL, CDCl$_3$) δ1.08 [6H, d, J=7 Hz, (CH$_3$)$_2$CH], 1.30 (3H, t, J=7 Hz, CH$_3$CH$_2$O), 2.15 (3H, d, J=1.5 Hz, CH$_3$C=), 4.15 (2H, q, J=7 Hz, CH$_3$CH$_2$O), 5.68 (1H, br.s, CH=C); IR (neat) 1705 (C=O), 1640 (C=C), 1385 and 1365 [(CH$_3$)$_2$C] cm$^{-1}$; GLC (2% OV-17, Chrom W 80/100, 2 mm×200 cm, 60° C., N$_2$ 30 cc/m) retention time, 9 min.

EXAMPLE III

3,4-Dimethyl-2-pentenoic acid (X)

A mixture of aqueous potassium hydroxide solution (0.5 N, 92 mL) and ethyl 3,4-dimethyl-2-pentenoate (XI, 5.5 g) was stirred at 80° C. for 17 hours until the oily supernatent layer disappeared. The reaction mixture was cooled, acidified with aqueous sulfuric acid, (0.5 N, ca. 100 mL), and extracted with ether. The ethereal layer was washed with water, dried over anhydrous magnesium sulfate, filtered, and evaporated under reduced pressure to afford 3,4-dimethyl-2-pentenoic acid as a yellow liquid (X, 4.1 g, 91%).

EXAMPLE IV

3,4-Dimethyl-2-pentenoylchloride (IX)

3,4-Dimethyl-2-pentenoic acid (XI, 4.1 g) was heated to a gentle boil with thionyl chloride (50 g) in benzene (50 mL) until the generation of hydrochloric acid gas ceased. Removal of the excess thionyl chloride and benzene by evaporation in vacuo followed by a distillation of the reaction product gave pure 3,4-dimethyl-2-pentenoylchloride (IX, 64° C. (9.5 mm)).

EXAMPLE V

3-(3',4'-Dimethyl-2'-pentenoyl) bruceolide (IV) and 3,15-di(3',4'-dimethyl-2'-pentenoyl) bruceolide (III)

A solution of 3,4-dimethyl-2-pentenoylchloride (IX, 329 mg, 2.23 mmol) in dry chloroform (4 mL) was added dropwise to a solution of bruceolide (II, 207 mg, 0.47 mmol) in dry pyridine (4 mL) at 0° C. The mixture was stirred at 56° C. for 24 hours. After cooling, the reaction mixture was acidified with dilute aqueous sulfuric acid and the product extracted with chloroform. The chloroform layer was dried over anhydrous magnesium sulfate, filtered, and evaporated under reduced pressure to give a brown viscous oil. This oil was purified by preparative thin layer chromatography [chloroform-acetone (10:1, v/v)] to yield 3,15-di(3',4'-dimethyl-2'-pentenoyl) bruceolide (III, [α]$_D^{25}$ −25° (c 0.45, pyridine) yield 47%) and 3-(3',4'-dimethyl-2'-pentenoyl) bruceolide (IV, white crystals 79.91 mg, yield 31%).

Compound (IV) was converted to (III) in 77% yield by esterification with 3,4-dimethyl-2-pentenoyl chloride in accordance with the procedure described above. The relevant NMR and mass spectral data of (III) and (IV) as well as bruceantin V are described in Table I below.

In accordance with the above procedure, but where, in place of 3,4-dimethyl-2-pentenoyl chloride, there is utilized benzoyl chloride, trimethoxybenzoyl chloride or cinnamoyl chloride there is obtained the corresponding 3-ester or 3,15-diester. Similarly, but where, in place of bruceolide, there is utilized brusatol and as an acid chloride there is utilized succinoyl chloride, glutaroyl chloride and acetyl chloride, there is obtained 3,3-bis-brusatolyl succinate, 3,3-bisbrusatolyl glutarate and 3,11,12-brusatolyl triacetate, 3, 11, 12 bis brusatolyl triacetate can also be prepared by acetylation with pyridine in acetic anhydride.

TABLE I

Relevant $^1$H NMR$^a$ and Mass$^b$ Spectral Data of the Products

| Signal | Compd III | IV | V |
|---|---|---|---|
| H-11 | 4.24 (m) | 4.20 (m) | 4.26 (m) |
| H-12 | 4.20 (m) | 4.20 (m) | 4.22 (m) |
| H-15 | 6.21 (d,13$^c$) | 5.29 (d,13$^c$) | 6.26 (d,13$^c$) |
| H-22 | 5.64 (m) | — | 5.65 (m) |
| Me-23 | 2.15 (bs) | — | 2.16 (bs) |
| Me-25 | 1.06 (d,6.5$^c$) | — | 1.07 (d,6.5$^c$) |
| H-29 | 5.90 (m) | 5.88 (m) | — |
| Me-30 | 2.15 (bs) | 2.12 (bs) | — |
| Me-32 | 1.09 (d,6.5$^c$) | 1.09 (d,6.5$^c$) | — |
| 658 (m/e) | 0.6% (M$^+$) | — | — |
| 548 (m/e) | 0.9% | 0.5% (M$^+$) | 3.7% (M$^+$)$^d$ |
| 111 (m/e) | 100% | 100% | 100% |

$^a$δ values (ppm) relative to TMS in CDCl$_3$ solution.
$^b$m/e values and their relative intensity in EI mass spectra.
$^c$Coupling constant in Hz.
$^d$Observed m/e 548.2250 (calcd for C$_{28}$H$_{36}$O$_{11}$, 548.2256) and 111.0807 (calcd for C$_7$H$_{11}$, 111.0809).

EXAMPLE VI

Bruceantin V

To a solution of 3,15-di(3',4'-dimethyl-2'-pentenoyl bruceolide (III, 78.3 mg, 0.119 mmol) in methanol (16 mL) was added p-toluenesulfonic acid (240 mg, 1.26 mmol). The mixture was heated under reflux and the reaction followed by thin layer chromatography (chloroform-acetone, 1:1). After 92 hours, it was purified by preparative thin layer chromatography (chloroform-acetone, 1:1) to yield bruceantin (V, 26.9 mg, 41.3%) as white crystals. Further purification of these white crystals by HPLC [chloroformethylacetate (1:1), Whatman partisil M 9 10/50] gave 98% pure bruceantin: mp 220°–223° C. (lit. mp 225°–226°); [α]$_D^{25}$ −31.6° (c 0.5, pyridine) [Lit. [α]$_D^{25}$ −43° (c 0.31, pyridine)]. The identity of bruceantin was confirmed by a direct comparison (mmp, TLC, IR, NMR, and mass spectra) with an authentic sample of bruceantin. In addition to bruceantin, unreacted diester (III, 10.9 mg, 14%) and bruceolide (II, 6.5 mg, 13%) were also isolated from this reaction product by preparative thin layer chromatography (chloroform-acetone, 1:1).

In accordance with the foregoing procedure, but where, in place of 3,15-di(3',4'-dimethyl-2'-pentenoyl) bruceolide (III), there is utilized 3,15-di(benzoyl-, trimethoxybenzoyl-, or cinnamoyl) bruceolide, there is obtained the corresponding 15-bruceolide ester.

EXAMPLE VII

15-Desenecioyl bruceoside-A (VI)

A mixture of bruceoside-A (I, 692.3 mg, 1.16 mmol) and methanolic potassium hydroxide (1 N, 21 mL) was stirred at room temperature for six hours. The mixture was neutralized with cation exchange resin (Dowex 50 W-X2) and filtered. The filtrate was methylated with diazomethane in the usual manner. The methylated product was evaporated in vacuo and purified by preparative thin layer chromatography (chloroform-methanol-water, 50:14:3) to yield 15-desenecioyl bruceoside-A (VI, 184.2 mg, 57.3% yield) as an amorphous substance which decomposed at ca. 200° C. IR: 3400, 1065 and 1040 cm$^{-1}$, 13C-NMR: 102.0 (C-1') and anomeric carbon 195.1 (C-3, C=O) 173.6, 172.7 (C-16 & C-18 C=O) and 130.1 (c-1, c=c); mass. spec. (trimethylsilyl ether) 271.1184 (calcd for $C_{12}H_{23}O_3Si_2$: 271.1184) and 361 ($C_{15}H_{33}O_4Si_3$) (trimethylsilyl ether of the sugar moiety).

In accordance with the above procedure but where, in place of bruceoside-A, there is utilized bruceoside-B, the corresponding 15-desenecioyl compound is obtained.

EXAMPLE VIII

Preparation of 15-desenecioyl bruceoside-A 15-(3',4'-dimethyl-2'-pentenoate) (VII) and acid hydrolysis to bruceantin (V)

A solution of 15-desenecioyl bruceoside-A (VI, 89.9 mg, 0.15 mmol) in dry pyridine (2 mL) was added dropwise to a solution of 3,4-dimethyl-2-pentenoyl chloride (IX, 330 mg, 2.25 mmol) in dry chloroform (2 mL). The mixture was stirred at room temperature for 20 hours until the thin layer chromatography (chloroform-methanol-water, 50:14:3) showed the disappearance of (VI), water was then added to decompose the unreacted acid chloride. The reaction product without further purification and isolation, was dissolved in dichloromethane (10 mL), and then borontrifluoride etherate (six drops) added. The reaction mixture was stirred at room temperature and examined by thin layer chromatography (chloroform-acetone, 1:1). After 4 days, the product was subjected to preparative thin layer chromatography (chloroform-acetone, 10:1) to yield pure bruceantin (V, 47.7 mg, 58% yield).

In accordance with the above procedure but where in place of 3,4-dimethyl-2-pentenoyl chloride, there is utilized benzoyl chloride, trimethoxybenzoyl chloride or cinnamoyl chloride there is obtained the corresponding 15-benzoyl bruceolide, 15-trimethoxybenzoyl bruceolide and 15-cinnamoyl bruceolide.

EXAMPLE IX 15-(3'-Methyl-butanoyl)bruceolide, (dihydrobrusatol) (VIIIb)

Brusatol (VIIIa) is taken up in ethyl acetate and hydrogenated at atmospheric temperature and pressure in the presence of Palladium charcoal catalyst (10% Pd/c). Upon uptake of 1 mole/mole of hydrogen, the catalyst is removed by filtration, the solvent removed by evaporation, and the residue purified by preparative thin layer chromatography to yield dihydrobrusatol (VIIIb).

What is claimed is:

1. A compound of the formula

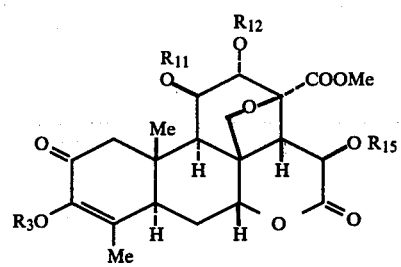

wherein R$_3$ is benzoyl, trimethoxybenzoyl, bruceantinyl malonyl, bruceantinyl succinoyl, bruceantinyl glutaroyl, and lower alkanoyl at 1 to 5 carbon atoms, brusatolyl malonyl, brusatolyl succinoyl, brusatolyl glutaroyl, R$_{15}$ is benzoyl, trimethoxybenzoyl, dihydrosenecioyl and lower alkanoyl 1 to 5 carbon atoms or senecioyl where R$_3$ is brusatolyl succinoyl or brusatolyl glutaroyl, R$_{11}$ and R$_{12}$ are hydrogen or lower alkanoyl of 1 to 5 carbon atoms.

* * * * *